(12) United States Patent
Seung et al.

(10) Patent No.: US 9,664,650 B2
(45) Date of Patent: May 30, 2017

(54) OMNI-DIRECTIONAL SHEAR-HORIZONTAL WAVE ELECTROMAGNETIC ACOUSTIC TRANSDUCER

(71) Applicant: Seoul National University R&DB Foundation, Seoul (KR)

(72) Inventors: Hong Min Seung, Seoul (KR); Yoon Young Kim, Seoul (KR)

(73) Assignee: SEOUL NATIONAL UNIVERSITY R & DB FOUNDATION, Seoul (KR)

(*) Notice: Subject to any disclaimer, the term of this patent is extended or adjusted under 35 U.S.C. 154(b) by 197 days.

(21) Appl. No.: 14/676,198

(22) Filed: Apr. 1, 2015

(65) Prior Publication Data

US 2016/0003779 A1    Jan. 7, 2016

(30) Foreign Application Priority Data

Jul. 2, 2014   (KR) .......................... 10-2014-0082535

(51) Int. Cl.
*G01N 29/24*    (2006.01)

(52) U.S. Cl.
CPC .  *G01N 29/2412* (2013.01); *G01N 2291/0422* (2013.01); *G01N 2291/0427* (2013.01)

(58) Field of Classification Search
CPC ....... G01N 29/2412; G01N 2291/0427; G01N 2291/0422
USPC .......................................................... 73/643
See application file for complete search history.

(56) References Cited

U.S. PATENT DOCUMENTS

| | | | | |
|---|---|---|---|---|
| 4,727,321 A * | 2/1988 | Huschelrath | ........... | G01N 27/82 324/226 |
| 5,525,849 A * | 6/1996 | Ito | ....................... | F16C 32/0438 310/90.5 |
| 6,600,399 B1 * | 7/2003 | Trandafir | ............... | H01F 7/066 335/222 |

(Continued)

FOREIGN PATENT DOCUMENTS

JP      2002095088 A      3/2002
JP      2003319493 A     11/2003

(Continued)

*Primary Examiner* — J M Saint Surin
(74) *Attorney, Agent, or Firm* — Cantor Colburn LLP

(57) ABSTRACT

A transducer is provided. The transducer includes: a permanent magnet unit formed in a form of a circular ring having upper and lower surfaces each having a predetermined diametrical direction width while having a circular through-portion in a central portion of the permanent magnet unit, the permanent magnet unit generating a vertical magnetic flux due to opposite magnetic poles that are formed in the upper and lower surfaces; and a coil wound in a diametrical direction across an area between an inner surface formed by the circular through-portion of the permanent magnet and an outer surface formed by an outer circumference of the permanent magnet and also wound in a circumferential direction of the permanent magnet, wherein the coil comprises a conductive material so that a current is applied to the coil, and when an alternating current is applied to the coil, a direction of the alternating current flowing along the coil and a direction of a magnetic field passing through the coil are orthogonal to each other.

7 Claims, 8 Drawing Sheets

(56) References Cited

U.S. PATENT DOCUMENTS

| | | | |
|---|---|---|---|
| 2005/0145042 A1* | 7/2005 | Ching-shun | G01D 5/145 73/862.331 |
| 2008/0093944 A1* | 4/2008 | Takahashi | H02K 1/2766 310/156.02 |
| 2012/0103097 A1* | 5/2012 | Lopez Jauregui | G01N 29/2412 73/643 |
| 2012/0240681 A1* | 9/2012 | Lopez Jauregui | G01N 29/043 73/643 |

FOREIGN PATENT DOCUMENTS

| | | |
|---|---|---|
| JP | 2007095846 A | 4/2007 |
| JP | 2012098226 A | 5/2012 |
| KR | 101061590 B1 | 8/2011 |

\* cited by examiner

OMNI-DIRECTIONAL SHEAR-HORIZONTAL WAVE ELECTROMAGNETIC ACOUSTIC TRANSDUCER

RELATED APPLICATION

This application claims the benefit of Korean Patent Application No. 10-2014-0082535, filed on Jul. 2, 2014, in the Korean Intellectual Property Office, the disclosure of which is incorporated herein in its entirety by reference.

BACKGROUND

1. Field

The inventive concept relate to a transducer, and more particularly, to an omni-directional shear-horizontal wave electromagnetic acoustic transducer.

2. Description of the Related Art

Since omni-directional transducers may generate waves having the same magnitude and mode in all directions, when applying omni-directional transducers to phased array systems, it is possible to efficiently focus waves by using the same algorithm with respect to all directions. However, typical omni-directional transducers generally generate and measure Lamb waves, which have several limitations in comparison with shear-horizontal waves, fundamental mode (SH0 mode) of which has non-dispersive property. Accordingly, it is necessary to develop transducers capable of efficiently generating and measuring shear-horizontal waves.

CITED REFERENCE

Korean Patent Registration No. 10-1061590

SUMMARY

The inventive concept provides a transducer including: a permanent magnet unit formed in a form of a circular ring having upper and lower surfaces each having a predetermined diametrical direction width while having a circular through-portion in a central portion of the permanent magnet unit, the permanent magnet unit generating a vertical magnetic flux due to opposite magnetic poles that are formed in the upper and lower surfaces; and a coil wound in a diametrical direction across an area between an inner surface formed by the circular through-portion of the permanent magnet and an outer surface formed by an outer circumference of the permanent magnet and also wound in a circumferential direction of the permanent magnet, wherein the coil includes a conductive material so that a current is applied to the coil, and when an alternating current is applied to the coil, a direction of the alternating current flowing along the coil and a direction of a magnetic field passing through the coil are orthogonal to each other.

Additional aspects will be set forth in part in the description which follows and, in part, will be apparent from the description, or may be learned by practice of the presented embodiments.

According to one or more exemplary embodiments, a transducer includes: a permanent magnet unit formed in a form of a circular ring having upper and lower surfaces each having a predetermined diametrical direction width while having a circular through-portion in a central portion of the permanent magnet unit, the permanent magnet unit generating a vertical magnetic flux due to opposite magnetic poles that are formed in the upper and lower surfaces; and a coil wound in a diametrical direction across an area between an inner surface formed by the circular through-portion of the permanent magnet and an outer surface formed by an outer circumference of the permanent magnet and also wound in a circumferential direction of the permanent magnet, wherein the coil includes a conductive material so that a current is applied to the coil, and when an alternating current is applied to the coil, a direction of the alternating current flowing along the coil and a direction of a magnetic field passing through the coil are orthogonal to each other.

The predetermined diametrical direction width of the permanent magnet may be half a wavelength corresponding to a shear-horizontal wave having a frequency to be generated.

The permanent magnet unit may include: a first permanent magnet unit formed in a form of a circular ring having upper and lower surfaces each having a predetermined diametrical direction width while having a first circular through-portion in a central portion of the first permanent magnet unit, the first permanent magnet unit generating a vertical magnetic flux due to opposite magnetic poles that are formed in the upper and lower surfaces; and a second permanent magnet unit disposed inside the first circular through-portion and formed in a form of a circular ring having upper and lower surfaces each having a predetermined diametrical direction width and a predetermined area while having a second circular through-portion in a central portion of the second permanent magnet unit, the second permanent magnet unit having an outer diameter corresponding to an inner diameter of the first circular through-portion and generating a vertical magnetic flux due to opposite magnetic poles that are formed in the upper and lower surfaces, wherein the coil is wound in the diametrical direction across an area between an inner surface formed by the second circular through-portion and an outer surface formed by an outer circumference of the first permanent magnet unit, and a surface of the first permanent magnet unit and a surface of the second permanent unit, which have different magnetic poles, are positioned on the same oriented surface so as to have magnetic flux in opposite directions.

A diametrical direction width of the first permanent magnet unit may be equal to a diametrical direction width of the second permanent magnet unit.

A diametrical direction width of the first permanent magnet unit, a diametrical direction width of the second permanent magnet unit, and a diameter of the second circular through-portion may be equal to each other.

The coil may include: a first winding portion crossing a circular ring; and a second winding portion crossing the circular ring in the diametrical direction as the first winding portion in the state in which the second winding portion extends from the first winding portion in a circumferential direction in an outer circumference portion of the circular ring and thus is spaced apart by a predetermined distance from the first winding portion.

The coil may be wound at regular intervals while having the same angle in the circumferential direction of the permanent magnet.

The transducer may further include a fixing unit attached to the permanent magnet, wherein the fixing unit includes an adhesive to fix the position of the coil.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
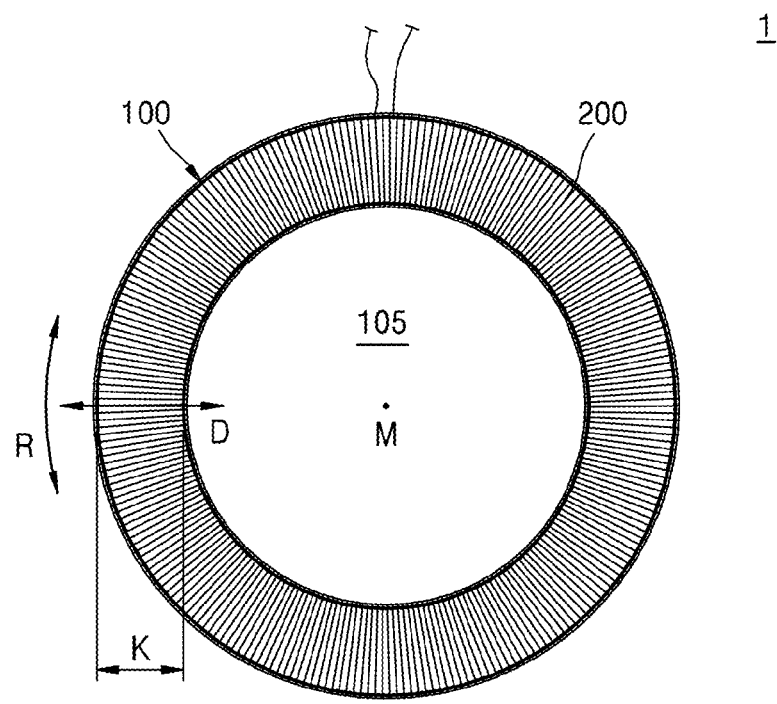
FIG. 1 is a view illustrating a transducer according to an exemplary embodiment of the inventive concept.

Hereinafter, exemplary embodiments of the inventive concept will be described in detail with reference to the attached drawings. The embodiments are not intended to be limitative.

Advantages, features, and a method of achieving the same will be specified with reference to embodiments that will be described in detail with reference to the attached drawings. However, the inventive concept will not be limited to the embodiments described below and may be embodied in various different forms. Merely, the exemplary embodiments are provided to perfectly disclose the inventive concept and to allow one of ordinary skill in the art to fully understand the inventive concept. The inventive concept is defined by the scope of claims thereof. Through the entire specification, like reference numerals designate like elements.

Expressions of "the left", "the right", and "the side", which are spatially relative, may be used to easily disclose correlations between one element or component and another element or component as shown in the drawings. The expressions spatially relative will be understood as terms including mutually different directions of an element when being used or operated, in addition to directions shown in the drawings. For example, when an element shown in the drawing overlies, "a vertical direction" may be understood as "a lateral direction". Accordingly, an exemplary term "vertical" may include "lateral". An element may be oriented a different direction in such a way that spatially relative terms may be understood according to an orientation thereof.

Additionally, the term "orthogonal" includes cases of being substantially orthogonal in addition to cases of being definitely orthogonal and will be understood as including a margin of error within a commonsensical range. Also, the term "omni-direction" will be understood as being substantially omni-directional and will not be understood as being limited to cases of being surely omni-directional.

Terms are used in the specification to describe the embodiments but not to limit the scope of the inventive concept. In the specification, a singular form includes a plural form if there is no particular mention. "Comprises" and/or "comprising" used in the specification do or does not exclude the existence or addition of one or more other elements, steps, operations, and/or devices in addition to an element, a step, an operation, and/or a device, which are mentioned.

If there is no other definition, all terms used in the specification, including technical and scientific terms, may be used as meanings capable of being understood to those skilled in the art in common. Also, terms defined in dictionaries generally used will not be ideally or excessively understood if not clearly and particularly defined.

In the drawings, thicknesses or sizes of respective elements are exaggerated, omitted, or schematically illustrated for convenience and clarity of description. Also, sizes and areas of respective elements do not completely reflect real sizes or real areas thereof.

Also, angles and directions mentioned while describing a structure in the embodiment are based on the drawings. In the specification, when not clearly mentioning a reference and relations of position with respect to an angle in a description on the structure, it is necessary to refer to a related drawing.

Figure 2:
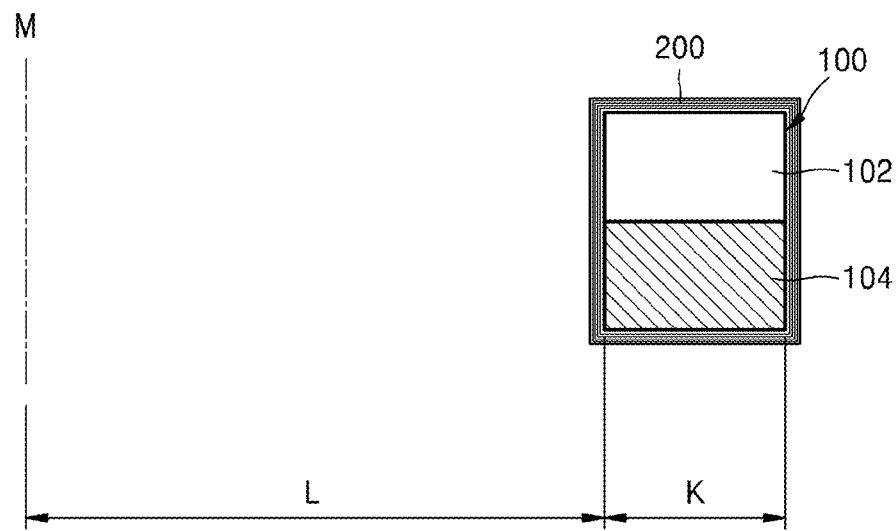
FIG. 2 is a cross-sectional view of the transducer of FIG. 1, according to an exemplary embodiment of the inventive concept.
Figure 3:
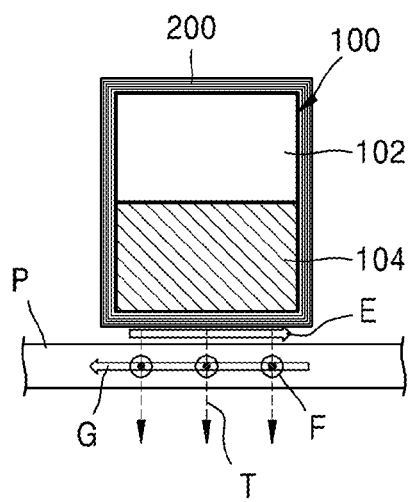
FIG. 3 is a view illustrating a magnetic flux, a current direction, an eddy direction, and a Lorentz force of the transducer of FIG. 1, according to an exemplary embodiment of the inventive concept.

FIG. 1 is a view illustrating a transducer 1 according to an exemplary embodiment of the inventive concept. FIG. 2 is a cross-sectional view of the transducer 1 of FIG. 1, according to an exemplary embodiment of the inventive concept. FIG. 3 is a view illustrating a magnetic flux, a current direction, an eddy direction, and a Lorentz force of the transducer 1 of FIG. 1, according to an exemplary embodiment of the inventive concept.

Referring to FIG. 1, the transducer 1 includes a permanent magnet 100 and a coil 200. The permanent magnet unit 100 is formed in the form of a circular ring having upper and lower surfaces each having a predetermined diametrical direction width (i.e., a predetermined width K in the diametrical direction D of the permanent magnet unit 100) while having a circular through-portion 105 in the central portion of the permanent magnet unit 100, and generates a vertical magnetic flux due to opposite magnetic poles that are formed in the upper and lower surfaces. The coil 200 is wound in the diametrical direction D across an area between an inner surface formed by the circular through-portion 105 of the permanent magnet 100 and an outer surface formed by the outer circumference of the permanent magnet 100 and winding-extends in the circumferential direction R of the permanent magnet 100.

The coil 200 includes a conductive material so that a current may be applied to the coil 200. When an alternating current is applied to the coil 200, the direction of the alternating current flowing along the coil 200 and the direction of a magnetic field passing through the coil 200 are orthogonal to each other.

As described above, the circular through-portion 105 is formed in the central portion 105 of the permanent magnet 100 having a circular outer portion, and thus, the permanent magnet 100 has the form of a circular ring including a circular hole. Accordingly the permanent magnet 100 has the diametrical direction D and the circumferential direction R, as shown in FIG. 1. The circular outer portion of the permanent magnet 100 is formed to have a predetermined width K in the diametrical direction D and a predetermined area. Accordingly, the permanent magnet 100 has circular ring-shaped upper and lower surfaces, a circular outer surface formed by the outer circumference, and a circular inner surface formed by the circular through-portion 105.

As illustrated in FIG. 2, as the permanent magnet 100 has the circular ring shape, the permanent magnet 100 may have the central point M and the circular through-portion 105 may have a predetermined radius L. In this case, the width K of the permanent magnet 100 and the radius L of the circular through-portion 105 may have a predetermined ratio therebetween. For example, when a wavelength of a shear-horizontal wave generated by the transducer 1 is $\lambda$, the width K may be $\frac{1}{2}\lambda$ and the radius L may be $\frac{3}{4}\lambda$.

In the permanent magnet 100, opposite magnetic poles are each formed in the upper surface and the lower surface. That is, a first pole 102 and a second hole 104 may be formed in the upper surface and the lower surface, respectively. The first pole 102 may be an N-pole, and the second pole 104 may be an S-pole. Accordingly, when the N-pole is formed in the upper surface and the S-pole is formed in the lower surface, a magnetic flux having a vector component going out in the upward direction is formed in the upper surface and a magnetic flux having a vector component coming in the upward direction from the lower side is formed in the lower surface. As described above, the upper surface and the lower surface may be differently interpreted according to the orientation and time, and thus are not limited to a specific direction and surface.

The coil 200 that is wound around the permanent magnet 100 is prepared. As described above, the coil 200 is wound in the diametrical direction D across an area between the inner surface formed by the circular through-portion 105 of the permanent magnet 100 and the outer surface formed by the outer circumference of the permanent magnet 100 and winding-extends in the circumferential direction R of the permanent magnet 100. The winding-extending means that a coil extends clockwise or counterclockwise along the permanent magnet 100 while being wound. That is, the coil 200 is wound around the permanent magnet 100, based on the center of the permanent magnet 100 having the circular ring shape, and is wound with angular displacement in the circumferential direction of the permanent magnet 100. Accordingly, the coil 200 extends in the diametrical direction D of the permanent magnet 100 on the upper surface and lower surface of the permanent magnet 100, and extends in the upward and downward direction on the outer circumference and inner circumference of the permanent magnet 100.

The coil 200 includes a conductive material so that a current may be applied thereto. That is, the coil 200 is formed of, for example, a copper wire so that a current may flow thereto. Accordingly, both ends of the coil 200 extend to the outside and may be connected to a power supplier.

When an alternating current is applied to the coil 200, the direction of the alternating current flowing along the coil 200 and the direction of a magnetic field passing through the coil 200 are orthogonal to each other.

That is, referring to FIG. 3, since the coil 200 is wound around the permanent magnet 100 as described above, the direction of a current E flowing through the coil 200 is the diametrical direction D of the permanent magnet 100 on the upper and lower surfaces of the permanent magnet 100. As described above, in the permanent magnet 100, a vertical magnetic flux T is formed since respective magnetic poles are formed in the upper surface and the lower surface, and a vector direction in which the magnetic flux T is formed is orthogonal to a vector direction of the current E flowing through the coil 200.

When using the transducer 1, an alternating current, i.e., the current E, is applied to the coil 200. When the transducer 1 is positioned on a conductive plate P and the alternating current E is applied to the coil 200, an eddy current G flowing in a direction opposite to the direction of the alternating current E occurs in the conductive plate P. Since the direction of the eddy current G is opposite to the direction of the alternating current E, the eddy current G flows in the diametrical direction D of the permanent magnet 100, like the alternating current E, and thus, the direction of the alternating current E is orthogonal to the direction of the magnetic flux T that is generated by the permanent magnet 100 and passes through the conductive plate P.

Figure 8:
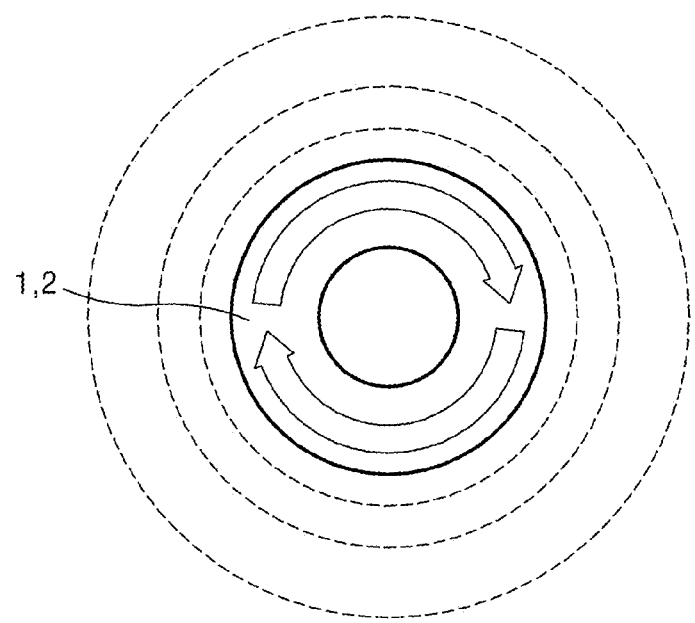
FIG. 8 is a view illustrating an omni-directional shear-horizontal wave generated by the transducer of FIG. 1 or FIG. 4, according to an exemplary embodiment of the inventive concept.

Accordingly, the eddy current G and the magnetic flux T generate a Lorentz force F. In this case, when the conductive plate P is positioned on the lower surface of the transducer 1, the alternating current E and the eddy current G flow in the diametrical direction of the permanent magnet 100 and the magnetic flux T induced by the permanent magnet 100 is formed in a direction passing through the conductive plate P, and thus, the Lorentz force F is formed in an area direction of the conductive plate P inside the conductive plate P. Since the coil 200 is wound around the permanent magnet 100 as described above, the Lorentz force F occurs in a circular form such as the form of the permanent magnet 100. For example, the Lorentz force F occurs in a form as shown in FIG. 8. Accordingly, the Lorentz force F generates a shear-horizontal force in an omni-direction, that is, in all directions.

For example, when the lower surface of the permanent magnet 100 has an N-pole, the conductive plate P is positioned on the lower surface of the transducer 1, the direction of the alternating current E is a direction directing from the center of the permanent magnet 100 to the outside on the lower surface of the transducer 1, the Lorentz force F is formed in a clockwise direction and in a circular form as shown in FIG. 8, according to the direction of the magnetic flux T and the direction of the eddy current G.

The width of the permanent magnet 100 in the diametrical direction D may be half a wavelength corresponding to a frequency of a shear-horizontal wave to be generated.

Figure 4:
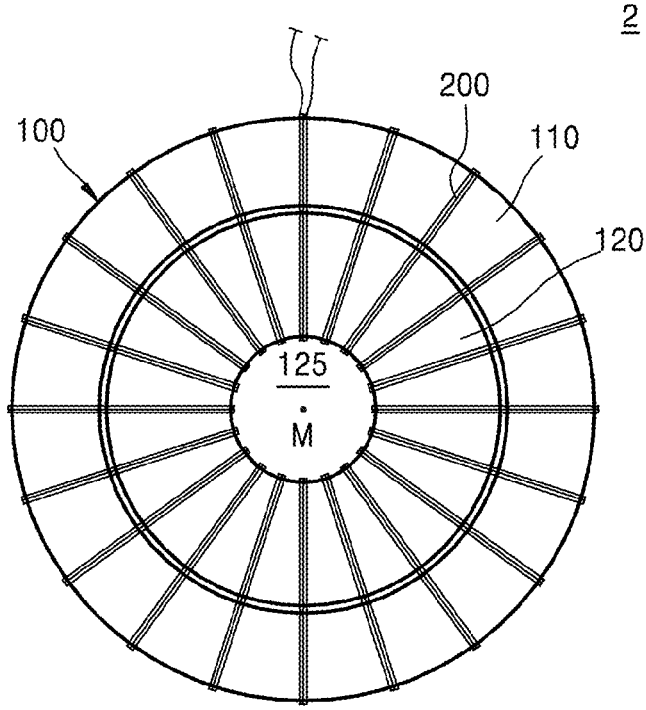
FIG. 4 is a view illustrating a transducer according to another exemplary embodiment of the inventive concept.
Figure 5:
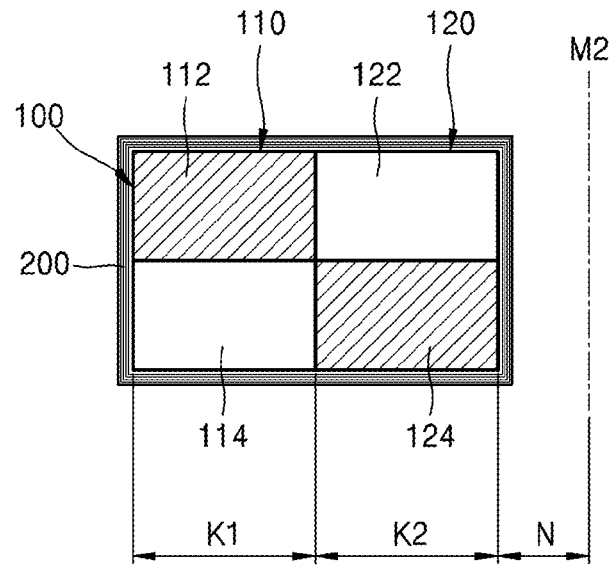
FIG. 5 is a cross-sectional view of the transducer of FIG. 4, according to another exemplary embodiment of the inventive concept.
Figure 6:
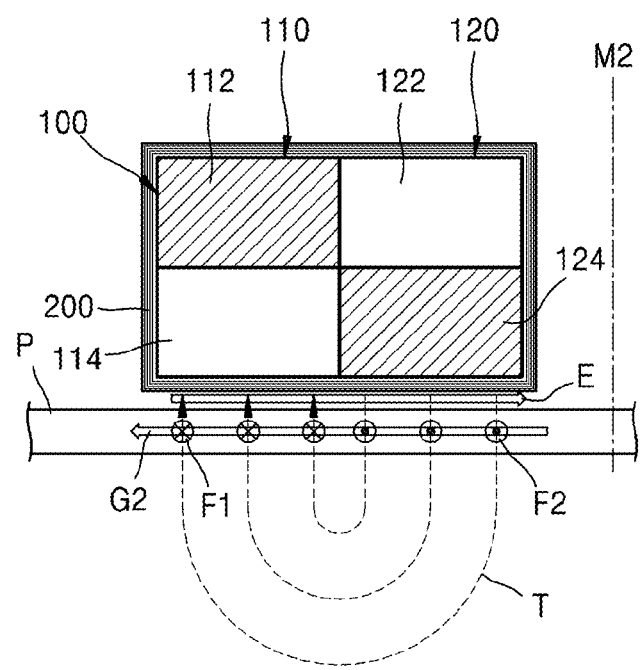
FIG. 6 is a view illustrating a magnetic flux, a current direction, an eddy direction, and a Lorentz force of the transducer of FIG. 4, according to another exemplary embodiment of the inventive concept.

FIG. 4 is a view illustrating a transducer 2 according to an exemplary embodiment of the inventive concept. FIG. 5 is a cross-sectional view of the transducer 2 of FIG. 4, according to an exemplary embodiment of the inventive concept. FIG. 6 is a view illustrating a magnetic flux, a current direction, an eddy direction, and a Lorentz force of the transducer 2 of FIG. 4, according to an exemplary embodiment of the inventive concept.

A permanent magnet 100 of the transducer 2 includes a first permanent magnet unit 110, a second permanent magnet unit 120, and a coil 200. The first permanent magnet unit 110 is formed in the form of a circular ring having upper and lower surfaces each having a predetermined diametrical direction width (i.e., a predetermined width in the diametrical direction of the first permanent magnet unit 110) while having a first circular through-portion in the central portion of the first permanent magnet unit 110, and generates a vertical magnetic flux due to opposite magnetic poles that are formed in the upper and lower surfaces. The second permanent magnet unit 120 is disposed inside the first circular through-portion, has an outer diameter corresponding to the inner diameter of the first circular through-portion, is formed in the form of a circular ring having upper and lower surfaces each having a predetermined diametrical direction width (i.e., a predetermined width in the diametrical direction) and a predetermined area while having a second circular through-portion 125 in the central portion of the second permanent magnet unit 120, and generates a vertical magnetic flux due to opposite magnetic poles that are formed in the upper and lower surfaces. The coil 200 is wound in the diametrical direction across an area between an inner surface formed by the second circular through-portion 125 and an outer surface formed by the outer circumference of the first permanent magnet unit 110. A surface of the first permanent magnet unit 110 and a surface of the second permanent unit 120, which have different magnetic poles, are positioned on the same oriented surface so as to have magnetic flux in opposite directions.

The first permanent magnet unit 110 and the second permanent magnet unit 120 have a similar structure to the permanent magnet 100 described above. That is, each of the first and second permanent units 110 and 120 has the form of a circular ring having a predetermined width in the diametrical direction so as to have upper and lower surfaces, and opposite magnetic poles are respectively formed in the upper surface and the lower surface. The first circular through-portion is formed in the central portion of the first permanent magnet unit 110, and the second circular through-portion 125 is formed the central portion of the second permanent magnet unit 120. Accordingly, the first permanent magnet unit 110 and the second permanent magnet unit 120 have a concentric structure and share the central point M2. Furthermore, the first permanent magnet unit 110 has a first pole 112 and a second pole 114 which are different magnetic poles, and the second permanent magnet unit 120 has a first pole 122 and a second pole 124 which are different magnetic poles.

The second permanent magnet unit 120 is inserted in the first circular through-portion of the first permanent magnet unit 110. That is, the inner diameter of the first circular through-portion may have a size corresponding to the outer diameter of the second permanent unit 120 so that the second permanent magnet unit 120 is disposed inside the first circular through-portion of the first permanent magnet unit 110.

As described above, a surface of the first permanent magnet unit 110 and a surface of the second permanent unit 120, which have different magnetic poles, are positioned on the same oriented surface so as to have magnetic flux T in opposite directions. For example, when the second permanent magnet unit 120 is inserted in the first circular through-portion, a surface of the first permanent magnet unit 110 and a surface of the second permanent unit 120, which are positioned on the same oriented surface, have different magnetic poles. The oriented surface may designate the upper surface or lower surface of a combined structure of the first and second permanent magnet units 110 and 120, which is formed by inserting the second permanent magnet unit 120 in the first magnet unit 110.

When considering the lower surface of the combined structure, as illustrated in FIG. 6, in the case that the second pole 114 of the first permanent magnet unit 110 is an S-pole, the second pole 124 of the second permanent magnet unit 120 is an N-pole. In this case, the magnet flux T proceeding from the second permanent magnet unit 120 directly downward is curved by 180° due to the disposition of different magnetic poles and is directed to the S-pole.

Accordingly, the direction of a Lorentz force F1 that is formed under the first permanent magnet unit 110 is opposite to the direction of a Lorentz force F2 that is formed under the second permanent magnet unit 120. When a conductive plate P is positioned under the transducer 2 including the permanent magnet 100 having the above-described structure and an alternating current is applied to the coil 200, an eddy current G2 is generated in the conductive plate P. In this case, the direction of the eddy current G2 is orthogonal to the magnetic flux T induced by the first permanent magnet unit 110 and the magnetic flux T induced by the second permanent magnet unit 120, and the direction of the magnetic flux T induced by the first permanent magnet unit 110 is opposite to the direction of the magnetic flux T induced by the second permanent magnet unit 120. Thus, the direction of the Lorentz force F1 is opposite to the direction of the Lorentz force F2. Furthermore, since the Lorentz forces F1 and F2 are applied in a circular form along the permanent magnet 100 as described above and the direction of the Lorentz force F1 induced by the first permanent magnet unit 110 is opposite to the direction of the Lorentz force F2 by the second permanent magnet unit 120, one of the Lorentz forces F1 and F2 has a clockwise direction and the other has a counterclockwise direction. For example, as shown in FIG. 6, when the direction of the Lorentz forces F1 induced by the first permanent magnet unit 110 may be a clockwise direction, the direction of the Lorentz forces F2 induced by the second permanent magnet unit 120 may be a counterclockwise direction, and vice versa.

Accordingly, since the transducer 2 generates the Lorentz forces F1 and F2 whose directions are opposite to each other and thus a torsional force is applied to the conductive plate P, the transducer 2 may generate a more strengthened omni-directional shear-horizontal wave.

A diametrical direction width K1 of the first permanent magnet unit 110 and a diametrical direction width K2 of the second permanent magnet unit 120 may be equal to each other, and the diametrical direction widths K1 and K2 may be each double the radius N of the second circular through-portion 125. That is, since the diametrical direction widths K1 and K2, which are equal to each other and are each double the radius N of the second circular through-portion 125, correspond to a half ($\frac{1}{2}\lambda$) of the wavelength of an omni-directional shear-horizontal wave that is generated by the transducer 2, a reinforced interference may occur and thus a more strengthened omni-directional shear-horizontal wave may be generated. The first permanent magnet unit 110 and the second permanent magnet unit 120 may adhere closely to each other.

Figure 7:
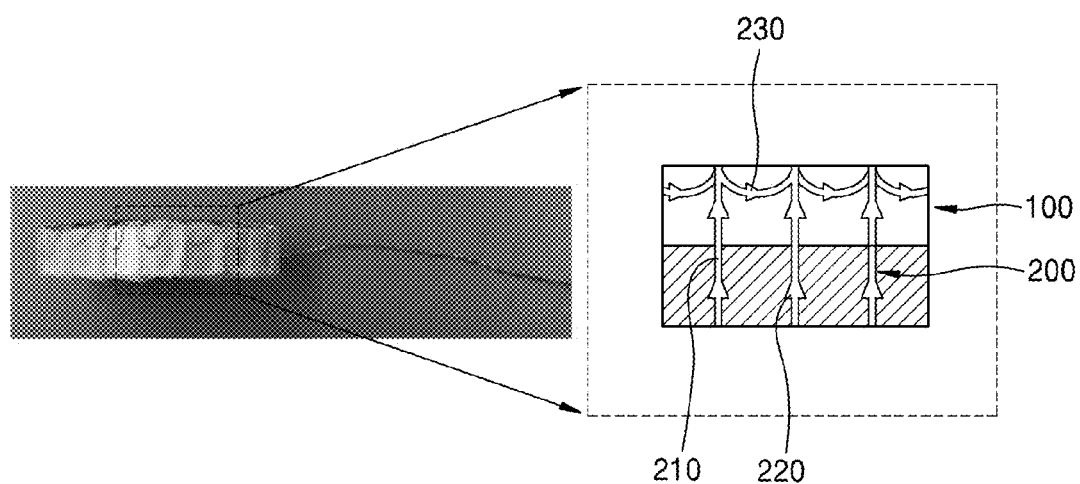
FIG. 7 is a view illustrating a form of the winding of a coil, according to an exemplary embodiment of the inventive concept.

FIG. 7 is a view illustrating a form of the winding of the coil 200, according to an exemplary embodiment of the inventive concept.

The coil 200 may include a first winding portion 210 crossing a circular ring, and a second winding portion 220 crossing the circular ring in the diametrical direction as the first winding portion 210 in the state in which the second winding portion 220 extends from the first winding portion 210 in a circumferential direction in the outer circumference portion of the circular ring and thus is spaced apart by a predetermined distance from the first winding portion 210.

In other words, as illustrated in FIG. 7, the coil 200 includes the first winding portion 210 and the second winding portion 220 that are each wound once across the circular ring of the permanent magnet 100 in the diametrical direction thereof. The first winding portion 210 and the second winding portion 220 are wound in the diametrical direction and are spaced apart from each other by a predetermined distance in the circumferential direction to have a predetermined angle therebetween. An arrow illustrated in FIG. 7 indicates the direction of a current.

The coil 200 include an extending portion 230 extending from the first winding portion 210 to the second winding portion 210 to wind the second winding portion 220 after winding the first winding portion 210. The extending portion 230 extends along the outer circumference portion of the permanent magnet 100 and moves a winding position, and may extend in a curved or straight line form. Accordingly, the first winding portion 210 of the coil 200 is wound at a position of the permanent magnet 100 and the second winding portion 220 of the coil 200 is wound at another position of the permanent magnet 100, and thus, by repeating such a process, the coil 200 may have a plurality of winding portions having a predetermined angle therebetween and thus may have a regular winding structure in the circumferential direction of the permanent magnet 100.

In this case, the extending portion 230 extending along the outer circumference portion of the permanent magnet 100 does not have an influence on a Lorentz force. That is, as the permanent magnet 100 has different magnetic poles in the vertical direction, a current flowing through the extending portion 230 is not positioned inside a magnetic flux and thus the extending portion 230 does not have an influence on a Lorentz force. Accordingly, the coil 200 may be uniformly wound without having an influence on a Lorentz force and may be wound at regular intervals in the circumferential direction of the permanent magnet 100.

A fixing unit may be disposed after winding the coil 200 at regular intervals. The fixing unit may be a member that is attached to the permanent magnet 100 and has adhesive strength. For example, the fixing unit may be formed of a member or component including a material having an adhesive strength, such as a cellophane tape or an adhesive. The fixing unit is coated on or attached to the surface of the permanent magnet 100 so that the coil 100 is fixed to a predetermined position and thus maintain the regular structure in which the coil 200 is wound at regular intervals.

Figure 9:
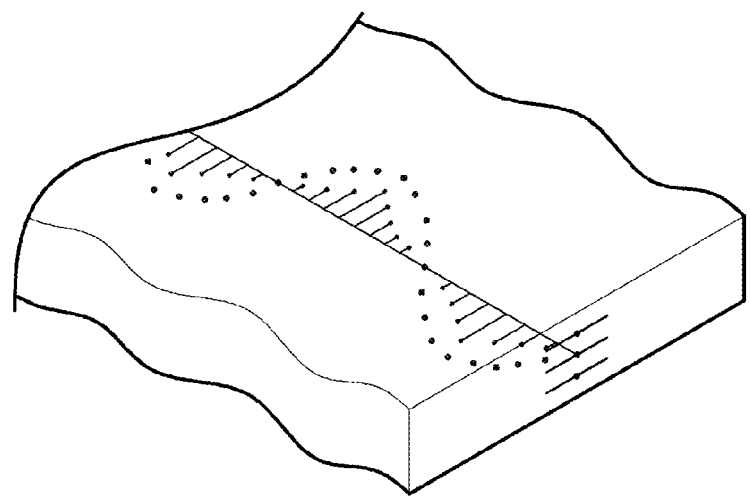
FIG. 9 is a view illustrating a waveform of a propagating shear-horizontal wave in a plate.
Figure 10:
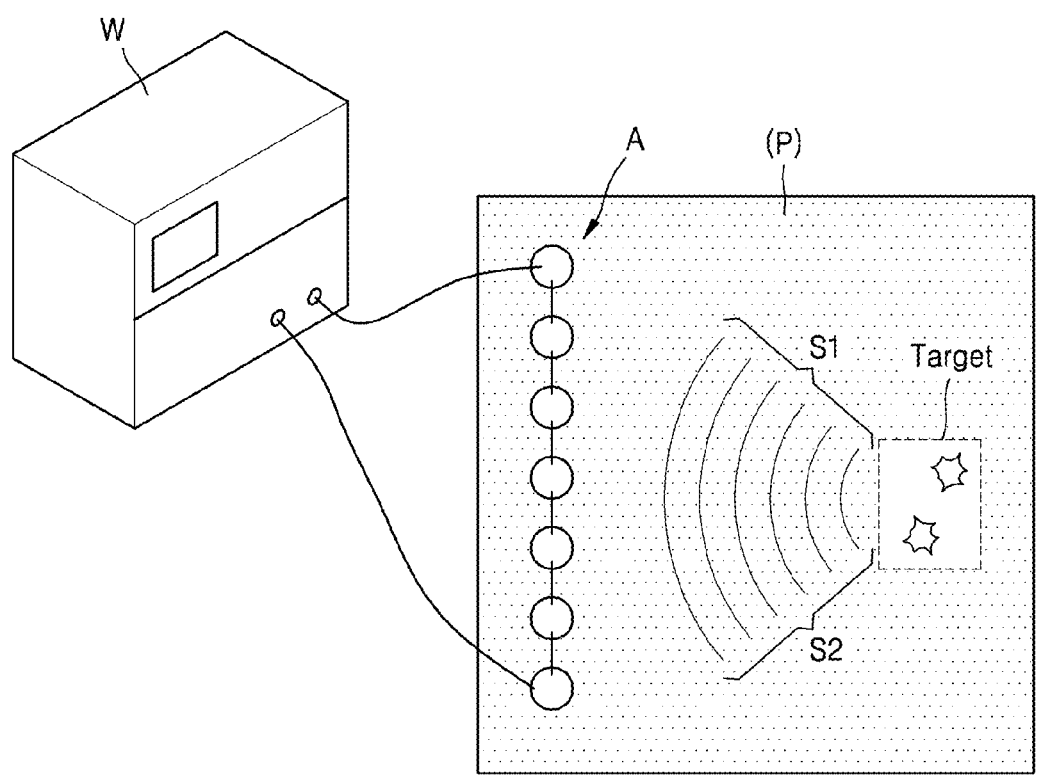
FIG. 10 is a view illustrating an inspection apparatus including the transducer of FIG. 1 or FIG. 4, according to an exemplary embodiment of the inventive concept.

FIG. 8 is a view illustrating an omni-directional shear-horizontal wave generated by the transducer 1 or 2, FIG. 9 is a view illustrating a waveform of a propagating shear-horizontal wave in a plate, and FIG. 10 is a view illustrating an inspection apparatus including the transducer 1 or 2, according to an exemplary embodiment of the inventive concept.

As shown in FIG. 8, the transducer 1 or 2 may generate a shear-horizontal wave in an omni-direction, that is, in all directions. The direction of the shear-horizontal wave may be a clockwise direction or a counterclockwise direction according to a magnetic pole of the permanent magnet 100, as described above.

As shown in FIG. 9, in the case of the shear-horizontal wave, a motion of a particle is polarized horizontally toward a surface of a medium in such a way that only in-plane deformation exists with respect to a plane formed by the direction of propagation and the direction of the motion of the particle.

The shear-horizontal wave may overcome dispersion properties according to a frequency, simultaneous existence of a symmetric mode and an anti-symmetric mode, and sensitivity to an effect caused by a surface load, which are defects of general Lamb waves. That is, it is possible to have the fundamental mode of shear-horizontal waves (SH0 mode) having non-dispersive properties, it is easy to use a single mode, and it is not sensitive to an effect of a surface load, thereby making up for the defects of Lamb waves.

Also, since the transducer 1 or 2 generates a shear-horizontal wave in all directions, an inspection may be easily and precisely performed and it is possible to configure a low-priced non-destructive examination apparatus having high efficiency.

Also, as described above, according to the excitation theory and the measurement theory, the transducer 1 or 2 may be used as an excitation source when applying current and may be used as a sensor when applying a shearing deformation.

The transducer 1 or 2 may uniformly generate an omni-directional shear-horizontal wave in a contactless method toward to a structure to perform the measurement thereof. The transducer 1 or 2 may more rapidly and efficiently investigate a wide inspection area by using the omni-directional shear-horizontal wave. Since conventional techniques use omni-directional Lamb waves or contact-type omni-directional shear-horizontal waves, there are disadvantages in which the defects of Lamb waves and problems occurring due to a contact between a structure and a transducer exist. On the contrary, when the transducer 1 or 2 generating an omni-directional shear-horizontal wave in a contactless method is used, an effective inspection may be performed in a contactless method while solving various defects of Lamp waves.

In addition, the performance of the transducer 1 or 2 may be improved by adjusting the magnetism of the permanent magnet 100 and the intensity of an input current, a more uniform eddy current may be applied to the permanent magnet 100 by adjusting the number of winding of the coil 200, and frequency characteristics may be changed by using magnets having various sizes.

As shown in FIG. 10, a plurality of transducers (i.e., the transducers 1 or 2) according to an exemplary embodiment of the inventive concept may be arranged on a plate P, and shear-horizontal waves may be generated toward a diagnostic area to diagnose damage to the diagnostic area or various kinds of fault conditions. 51 denotes a shear-horizontal wave generated by a transducer array A including the plurality of transducers, and S2 denotes a shear-horizontal wave reflected from the diagnostic area. However, the waveforms of the shear-horizontal waves are not limited to forms shown in FIG. 8. In this case, images and data of the diagnostic area may be formed by an apparatus W.

Figure 11:
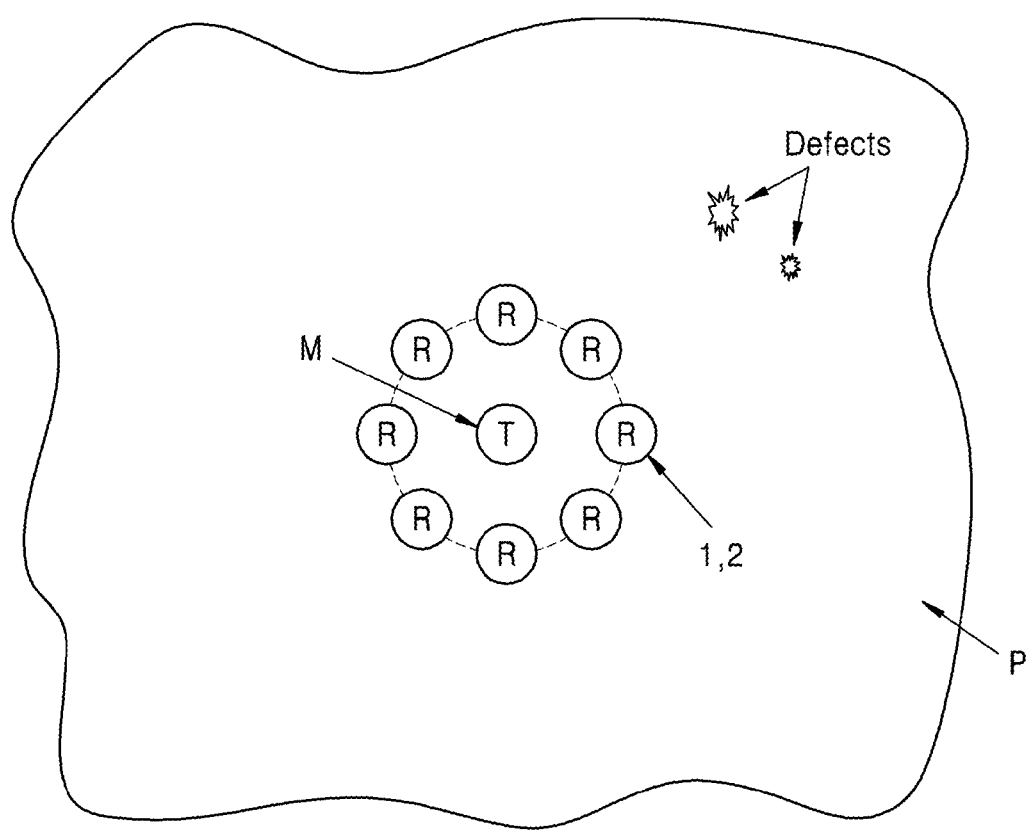
FIG. 11 is a view illustrating a diagnostic method using the transducer of FIG. 1 or FIG. 4, according to an exemplary embodiment of the inventive concept.

FIG. 11 is a view illustrating a diagnostic method using the transducer 1 or 2, according to an exemplary embodiment of the inventive concept.

As shown in FIG. 11, a single transmitter multiple receivers (STMR) structure may be configured by arranging a plurality of transducers (i.e., the transducers 1 or 2) according to an exemplary embodiment as receivers on a plate P and mounting a contact-type omni-directional shear-horizontal wave transducer M as a transmitter on the center of the plate P, and thus the entire area of the plate P may be diagnosed by using the STMR structure. In this case, since the transducers 1 or 2 that generate omni-directional shear-horizontal waves in a contactless method are used as the receivers, an error that may be generated by a contact-type transducer may be reduced and an interval between the transmitter and the receivers may be freely adjusted to diagnose the entire area of the plate P. In addition, the use of unnecessary channels and wires may be avoided since several points may be inspected even though only one receiver is used.

Figure 12A:
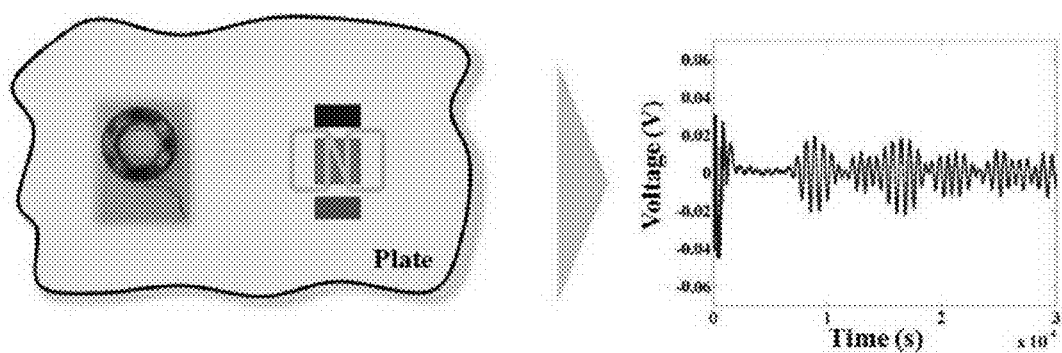
FIGS. 12A and 12B are graphs each illustrating an experimental result obtained by generating and measuring a shear-horizontal wave by using the transducer of FIG. 1, formed by using a single permanent magnet, in a conductive plate.
Figure 12B:
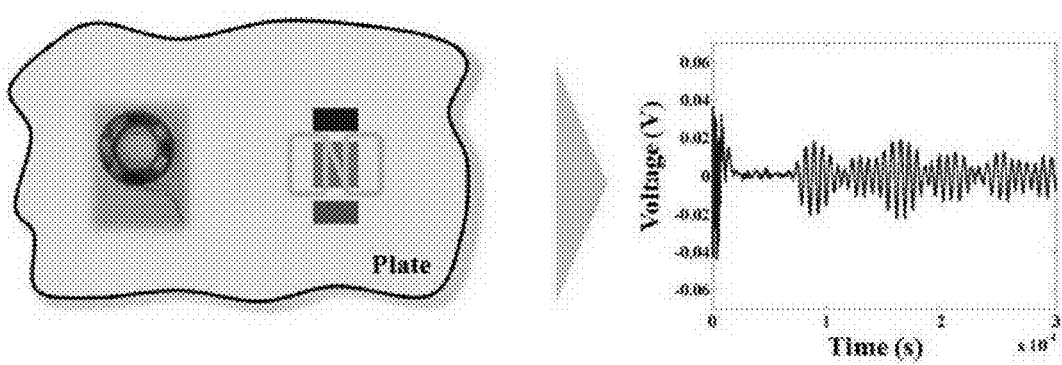

FIGS. 12A and 12B are graphs each illustrating an experimental result obtained by generating and measuring a shear-horizontal wave by using the transducer 1, formed by using a single permanent magnet, in a conductive plate.

FIG. 12A illustrates an experimental result obtained in the case that the transducer 1 mounted on the conductive plate in a contactless method is used as a transmitter and a contact-type shear-horizontal wave transducer mounted on the conductive plate is used as a receiver. FIG. 12B illustrates an experimental result obtained in the case that the transducer 1 is used as a receiver and the contact-type shear-horizontal wave transducer is used as a transmitter. In terms of the experimental results for the two cases, it may be understood that the transducer 1 may generate a shear-horizontal wave and measure the generated shear-horizontal wave.

Figure 13A:
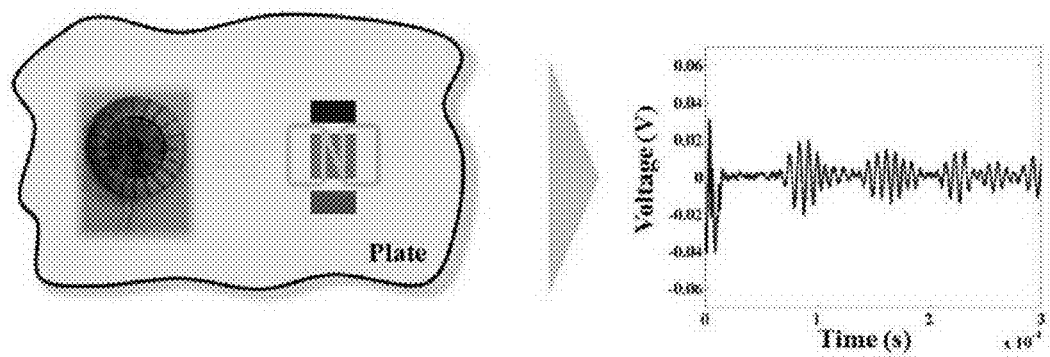
FIGS. 13A and 13B are graphs each illustrating an experimental result obtained by generating and measuring a shear-horizontal wave by using the transducer of FIG. 4, formed by using two permanent magnets, i.e., periodic permanent magnets, in a conductive plate.
Figure 13B:
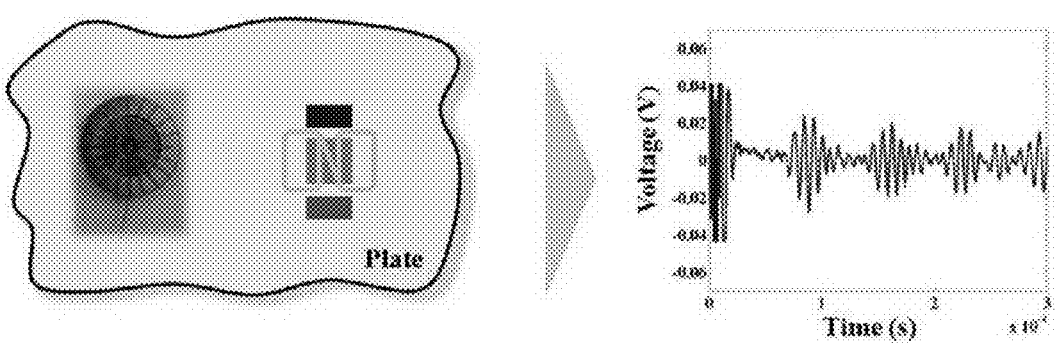

FIGS. 13A and 13B are graphs each illustrating an experimental result obtained by generating and measuring a shear-horizontal wave by using the transducer 2, formed by using two permanent magnets, i.e., periodic permanent magnets, in a conductive plate.

FIG. 13A illustrates an experimental result obtained in the case that the transducer 2 mounted on the conductive plate in a contactless method is used as a transmitter and a contact-type shear-horizontal wave transducer mounted on the conductive plate is used as a receiver. FIG. 13B illustrates an experimental result obtained in the case that the transducer 2 is used as a receiver and the contact-type shear-horizontal wave transducer is used as a transmitter. In terms of the experimental results for the two cases, it may be understood that the transducer 2 may generate a shear-horizontal wave and measure the generated shear-horizontal wave.

As described above, a transducer according to the one or more of the above exemplary embodiments may generate an omni-directional shear-horizontal wave and measure the omni-directional shear-horizontal wave. The shear-horizontal wave may overcome dispersion properties according to a frequency, simultaneous existence of a symmetric mode and an anti-symmetric mode, and sensitivity to an effect caused by a surface load, which are defects of general Lamb waves. That is, it is possible to have an SH0 mode having non-dispersive properties, it is easy to use a single mode, and it is not sensitive to an effect of a surface load, thereby making up for the defects of Lamb waves.

Also, the transducer may uniformly generate an omni-directional shear-horizontal wave in a contactless method toward a structure to perform the measurement thereof. The transducer 1 or 2 may more rapidly and efficiently investigate a wide inspection area by using the omni-directional shear-horizontal wave. Since conventional techniques use omni-directional Lamb waves or contact-type omni-directional shear-horizontal waves, there are disadvantages in which the defects of Lamb waves and problems occurring due to a contact between a structure and a transducer exist. On the contrary, when the transducer 1 or 2 generating an omni-directional shear-horizontal wave in a contactless method is used, an effective inspection may be performed in a contactless method while solving various defects of Lamp waves.

Accordingly, since the transducer generates a shear-horizontal wave in all directions, an inspection may be easily and precisely performed and it is possible to configure a low-priced non-destructive examination apparatus having high efficiency.

Also, the performance of the transducer may be improved by adjusting the magnetism of a permanent magnet in the transducer and the intensity of an input current, a more uniform eddy current may be applied to the permanent magnet by adjusting the number of winding of a coil in the transducer, and frequency characteristics may be changed by using magnets having various sizes.

Also, since the coil wound around the permanent magnet has a regular winding structure, the transducer may generate and measure a uniform shear-horizontal wave with respect to all directions.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A transducer comprising:
    a permanent magnet unit formed in a form of a circular ring having upper and lower surfaces each having a predetermined diametrical direction width while having a circular through-portion in a central portion of the permanent magnet unit, the permanent magnet unit generating a vertical magnetic flux due to opposite magnetic poles that are formed in the upper and lower surfaces; and
    a coil wound in a diametrical direction across an area between an inner surface formed by the circular through-portion of the permanent magnet and an outer surface formed by an outer circumference of the permanent magnet and also wound in a circumferential direction of the permanent magnet,
    wherein the coil comprises a conductive material so that a current is applied to the coil, and when an alternating current is applied to the coil, a direction of the alternating current flowing along the coil and a direction of a magnetic field passing through the coil are orthogonal to each other,
    wherein the permanent magnet unit comprises:
    a first permanent magnet unit formed in a form of a circular ring having upper and lower surfaces each having a predetermined diametrical direction width while having a first circular through-portion in a central portion of the first permanent magnet unit, the first permanent magnet unit generating a vertical magnetic flux due to opposite magnetic poles that are formed in the upper and lower surfaces; and
    a second permanent magnet unit disposed inside the first circular through-portion and formed in a form of a circular ring having upper and lower surfaces each having a predetermined diametrical direction width and a predetermined area while having a second circular through-portion in a central portion of the second permanent magnet unit, the second permanent magnet unit having an outer diameter corresponding to an inner diameter of the first circular through-portion and generating a vertical magnetic flux due to opposite magnetic poles that are formed in the upper and lower surfaces, wherein the coil is wound in the diametrical direction across an area between an inner surface formed by the second circular through-portion and an outer surface formed by an outer circumference of the first permanent magnet unit, and a surface of the first permanent magnet unit and a surface of the second permanent unit, which have different magnetic poles, are positioned on the same oriented surface so as to have magnetic flux in opposite directions.

2. The transducer of claim 1, wherein the predetermined diametrical direction width of the permanent magnet is half a wavelength corresponding to a shear-horizontal wave having a frequency to be generated.

3. The transducer of claim 1, wherein a diametrical direction width of the first permanent magnet unit is equal to a diametrical direction width of the second permanent magnet unit.

4. The transducer of claim 1, wherein a diametrical direction width of the first permanent magnet unit, a diametrical direction width of the second permanent magnet unit, and a diameter of the second circular through-portion are equal to each other.

5. The transducer of claim 1, wherein the coil comprises:
a first winding portion crossing a circular ring; and
a second winding portion crossing the circular ring in the diametrical direction as the first winding portion in the state in which the second winding portion extends from the first winding portion in a circumferential direction in an outer circumference portion of the circular ring and thus is spaced apart by a predetermined distance from the first winding portion.

6. The transducer of claim 1, wherein the coil is wound at regular intervals while having the same angle in the circumferential direction of the permanent magnet.

7. The transducer of claim 1, further comprising a fixing unit attached to the permanent magnet,
wherein the fixing unit comprises an adhesive to fix the position of the coil.

* * * * *